United States Patent
Haveri et al.

(10) Patent No.: US 7,752,886 B2
(45) Date of Patent: Jul. 13, 2010

(54) MEASURING GAS COMPONENTS TOGETHER WITH A PARAMAGNETIC GAS

(75) Inventors: Heikki Haveri, Huhmari (FI); Kurt Weckström, Esbo (FI)

(73) Assignee: General Electric Company, Schenectady, NY (US)

( * ) Notice: Subject to any disclaimer, the term of this patent is extended or adjusted under 35 U.S.C. 154(b) by 579 days.

(21) Appl. No.: 11/690,539

(22) Filed: Mar. 23, 2007

(65) Prior Publication Data

US 2007/0227230 A1 Oct. 4, 2007

(30) Foreign Application Priority Data

Mar. 29, 2006 (EP) .................... 06111897

(51) Int. Cl.
*G01N 29/02* (2006.01)
(52) U.S. Cl. .................... 73/24.01; 73/24.06; 73/25.02; 324/204
(58) Field of Classification Search ................ 73/24.01, 73/24.06, 25.02; 324/204
See application file for complete search history.

(56) References Cited

U.S. PATENT DOCUMENTS

| | | | |
|---|---|---|---|
| 3,584,499 A | 6/1971 | Hummel | |
| 4,403,186 A * | 9/1983 | Kotani et al. | ................ 324/204 |
| 4,563,894 A | 1/1986 | Karrer et al. | |
| 4,633,705 A | 1/1987 | Merilainen et al. | |
| 4,772,848 A * | 9/1988 | Hummel | ..................... 324/204 |
| 4,808,921 A | 2/1989 | Christensen et al. | |
| 4,860,574 A * | 8/1989 | Maeda et al. | ................ 324/204 |
| 6,430,987 B1 | 8/2002 | Stark | |
| 2002/0017124 A1 | 2/2002 | Dempster et al. | |

FOREIGN PATENT DOCUMENTS

| | | | | |
|---|---|---|---|---|
| DE | 3541341 A * | 6/1986 | ................. | 73/25.02 |
| JP | 56-54349 A * | 5/1981 | ................. | 324/201 |
| JP | 02 290550 A | 11/1990 | | |

* cited by examiner

Primary Examiner—Daniel S Larkin
(74) Attorney, Agent, or Firm—Global Patent Operation; Jonathan E. Thomas (57) ABSTRACT

The invention concerns a gas analyzer, which comprises: an electromagnet that has an air gap; a power source for supplying cyclically variable electrical current/voltage to said electromagnet; a sample gas conduit and a reference gas conduit opening into said air gap; an exit conduit communicating with said air gap for removing the intermixed sample and reference gases; pressure detecting microphone or microphones connected to said sample gas conduit and to said reference gas conduit for sensing gas pressures at a first acoustic measuring frequency in the respective conduits giving at least one acoustic pressure signal component; and electronics connected to said microphone(s) to receive said acoustic pressure signal component or components to form at least a first intermediate output signal describing content of a paramagnetic gas component in the sample gas.

21 Claims, 4 Drawing Sheets

$N_2O$ and He in Volume percentage of oxygen and referenced to N2 at different magnetic field frequencies. Length L1 of the pneumatic path 15 mm.

Fig. 3

Spectrum of the acoustic frequencies at pressure detecting microphones

Fig. 4

Output signal SS1 with different gas mixtures at the frequency of 164 Hz

Fig. 5

Output signal SS2 with different gas mixtures at the frequency of 1722 Hz

Fig. 6

Helium signal linearity at the frequency of 1722 Hz.

Fig. 7

N2O and He in volume percentage of oxygen and referenced to N2 at different magnetic field frequencies. Length L1 of the pneumatic path 34 mm.

MEASURING GAS COMPONENTS TOGETHER WITH A PARAMAGNETIC GAS

RELATED APPLICATIONS

This application relates to and claims the benefit of priority under 35 U.S.C. Section 119(a)-(d) and 365(a) to co-pending European Patent Application No.: 06111897.2, filed on Mar. 29, 2006, which is herein incorporated by reference in its entirety.

FIELD OF THE INVENTION

The invention concerns a gas analyzer and a method for detecting various gas components and measuring the contents of various gas components present in a gas mixture, using variable magnetic field in an air gap of an electromagnet and measuring the pressures in the sample gas conduit and the reference gas conduit connected to the air gap.

BACKGROUND OF THE INVENTION

Paramagnetic gas components can be analyzed in different ways in gap(s) of one or more magnets while using variable magnetic field(s) for instance. One such alternative is disclosed in the patent publication U.S. Pat. No. 6,430,987 describing an apparatus for measuring the proportion of a paramagnetic gas in a gas sample. For the purpose the apparatus comprises: a first modulatable magnetic field source with a first air gap; a second modulatable magnetic field source with a second air gap; a modulation source for outputting a modulation signal to the magnetic field sources; a reversing switch means, which connects the modulation source to the first magnetic field source and the second magnetic field source in alternation; a measuring element, located in the air gaps, for outputting a heat flow measurement signal, which measuring element comprises a thermocouple arrangement with at least one first connection point and one second connection point, the thermocouple arrangement being positioned such that the first connection point is located in the first air gap and the second connection point is located in the second air gap; an alternating current source, connected to the thermocouple arrangement, by which source the thermocouple arrangement is heated to an operating temperature that is elevated compared to the gas sample; a filter device, connected to the thermocouple arrangement, for filtering out periodic fluctuations from the heat flow measurement signal caused by the modulation of the magnetic field sources, the amplitude of the periodic fluctuations being a measure for the proportion of the paramagnetic gas in the gas sample. Accordingly, here the proportion of a paramagnetic gas component is analyzed with thermocouple(s) having at least two sensing points in two gaps of magnets to detect a change of thermal conductivity, but without a reference gas, i.e. only sample gas is fed in to the gaps. Other than paramagnetic gas components cannot be measured with this system.

Another alternative is to use e.g. a microphone to detect the pressure difference between the sample gas and the reference gas fed into one air gap of a magnet. For this purpose the patent publication U.S. Pat. No. 4,633,705 discloses a measuring cell for measuring the oxygen content of a gas mixture comprising: a member having a closed cavity therein; a sample gas conduit extending into said cavity for supplying sample gas to said measuring cell; a reference gas conduit extending into said cavity for supplying reference gas to said measuring cell; an exit conduit for removing gases from said cavity; an electromagnet positioned in said cavity, said electromagnet having a core with spaced opposing magnetic poles forming an air gap therebetween, said electromagnet being energizable by chopped direct current for establishing a magnetic field in said air gap, at least one of said magnetic poles having passages extending therethrough and opening into said air gap, said passages being connected to said gas conduits for supplying sample and reference gases to said gap; and pedestals mounted in said air gap adjacent the openings of said passages for guiding the gases for mixing in said air gap, said mixed gases being discharged into said cavity for removal via said exit conduit. Accordingly, this publication discloses the basic concept for analyzing the content of a paramagnetic gas component in a gas mixture utilizing the paramagnetic susceptibility. Patent publication U.S. Pat. No. 4,808,921 also describes an apparatus for determining the concentration of a paramagnetic gas by measuring its pressure when subjected to an AC magnetic field. Here the apparatus comprises an AC electromagnet with an almost closed ferromagnetic circuit, a permanent magnet and a gap, a chamber positioned within said gap inlet and outlet lines for the gas to be analyzed as well as a gas of known magnetic susceptibility and means for measuring differential gas pressures in the respective lines created when the gas to be analyzed and the gas of known magnetic susceptibility are subjected to a combined AC and DC magnetic field generated by the electromagnet having an AC current winding and the permanent magnet wherein the DC magnetic field is superimposed onto the AC magnetic field by the permanent magnet. According to this publication, the magnetic powers generate the stray field and vibrations that influences the microphones via their nickel membranes, which causes generation of a false signal at a frequency of $2\omega$, i.e. twice the measuring frequency, which false signals do not influence the measuring signal at the one measuring frequency $\omega$. These two publications disclose quite analogous ways for analyzing a paramagnetic gas component, like oxygen.

Non-paramagnetic gas components in a gas mixture are typically analyzed by measuring the optical absorption—dispersively or non-dispersively—they cause in a beam of radiation, which radiation can be visible light, but in most cases infrared radiation, or by measuring the amount of radiation, e.g. intensity of light, emitted from a chemiluminescent reaction between certain gas components. Of course wavelengths practical or available for the purpose are used. These optical analyzing methods are useful as such, but analyzing both paramagnetic and non-paramagnetic gas components from the same gas mixture requires complicated system, i.e. at least two different analyzers, one for the paramagnetic gas(es) and another for the non-paramagnetic gas(es).

SUMMARY OF THE INVENTION

It is a main object of the invention to attain a gas analyzer, with which it is possible to measure both the concentration of a paramagnetic gas component and the concentration of at least one non-paramagnetic gas component. It is a second object of the invention to attain this kind of gas analyzer, in which the concentrations of the plurality of gas components, i.e. both paramagnetic and non-paramagnetic gas components, could be determined using the same detectors or at least same type of detectors in the same measuring arrangement. It is a third object of the invention to attain this kind of gas analyzer, which operates quick enough, i.e. with so small time constant, that monitoring of breathing is possible. Furthermore the measuring principle should be as simple as possible, its measurement results as accurate as possible, and its implementation inexpensive.

According to the invention the objects are attained by utilizing at least one microphone to detect the pressure difference between a sample gas and a reference gas fed into one air gap of an electromagnet, whereupon there is maintained a cyclically variable magnetic field in the air gap. The reference gas can be any gas, but preferably it has a paramagnetic gas component, like oxygen, that is one of the gases the concentration of which is measured in the sample gas. Alternatively the reference gas can be one of the other gases, like $N_2$, $N_2O$ or He, the concentrations of which are measured in the sample gas. Later in this description the respective values of index N or index M are shown in parentheses ( ). According to the inventive concept, in general by summing N+1 (N=0, 1, 2 . . . ) alternating magnetic fields causing respectively N+1 (N=0, 1, 2 . . . ) first harmonic magnetic field frequencies it is possible to measure the oxygen content at the lowest N=0 magnetic field frequency, i.e. at the respective acoustic measuring frequency, but in addition it is at least possible to detect, but even to measure the gas content of N gases (N=1, 2 . . . ) other than oxygen at each corresponding N (N=1, 2 . . . ) first harmonic magnetic field frequency, i.e. at the respective acoustic measuring frequency and/or further at their subharmonic frequencies. On the other hand it is also possible to measure the oxygen content and the content of even three gases other than oxygen by summing only two alternating or cyclically variable magnetic fields having lower and higher first harmonic frequency components. Oxygen content is then measured at the first harmonic of the lower magnetic field frequency, i.e. at the respective acoustic measuring frequency, the first gas other than oxygen is measured at the first harmonic of the higher magnetic field frequency, i.e. at the respective acoustic measuring frequency and the other two gas contents are measured preferably at the first subharmonic frequencies of the first harmonic of the higher magnetic field frequency. Also other subharmonic frequencies are possible, which may enable the gas content measurement of a plurality of gases other than oxygen.

In both cases the content of each measured gas other than oxygen is proportional to the signal difference between the measured acoustic pressure signal at the first harmonic of the lowest frequency and the acoustic pressure signal at the first harmonic of the higher frequency or one of its subharmonic frequencies. The higher magnetic field frequencies, i.e. the corresponding acoustic measuring frequencies, used for measuring the content of the gas or gases other than oxygen are predetermined for each gas specifically, depending on the properties of the measured gas, but also the pneumatic construction of the gas analyzer.

According to the first aspect of the invention it is provided a gas analyzer, comprising: an electromagnet 5 that has spaced opposing magnetic poles forming an air gap 16 with a magnetic field therebetween; power source 60 for supplying cyclically variable electrical current/voltage to said electromagnet; a sample gas conduit 1 and a reference gas conduit 2 opening into said air gap, said sample gas being a gas mixture to be analyzed, and said reference gas having a known concentration of a predetermined gas component; an exit conduit 18, 19 communicating with said air gap for removing the intermixed sample and reference gases from said air gap with the magnetic field; pressure detecting microphone or microphones 3, 4 connected to said sample gas conduit 1 and to said reference gas conduit 2 for sensing gas pressures at a predetermined frequency $f_{A1}$ in the respective conduits, and giving at least one acoustic pressure signal component S1 and/or S2; and electronics 29 connected to said microphone(s) to receive said acoustic pressure signal component or components to form at least a first intermediate output signal $SI_{A1}$ describing content of a paramagnetic gas component in the sample gas. Especially said predetermined frequency is a first acoustic measuring frequency $f_{A1}$, and in said gas analyzer: said pressure detecting microphone(s) 3, 4 connected to said sample gas conduit 1 and to said reference gas conduit 2 are adapted for sensing gas pressures at a second predetermined acoustic measuring frequency $f_{A2}$, and giving at least a second acoustic pressure signal component S3 and/or S4; and said electronics 29 connected to said microphone(s) receive said second acoustic pressure signal component or components to form a second intermediate output signal $SI_{A2}$ including content data of a second gas component in the sample gas.

Said multi-frequency power source 60 supplies a chopped or alternating electrical current/voltage to said electromagnet, which electrical current/voltage is constituted of superimposed or harmonic frequencies producing magnetic field frequencies $f_{M(N+1)}$ in said air gap 16 of the electromagnet 5 respective at least to said first and second acoustic measuring frequencies $f_{A1}$, $f_{A2}$.

Figure 1:
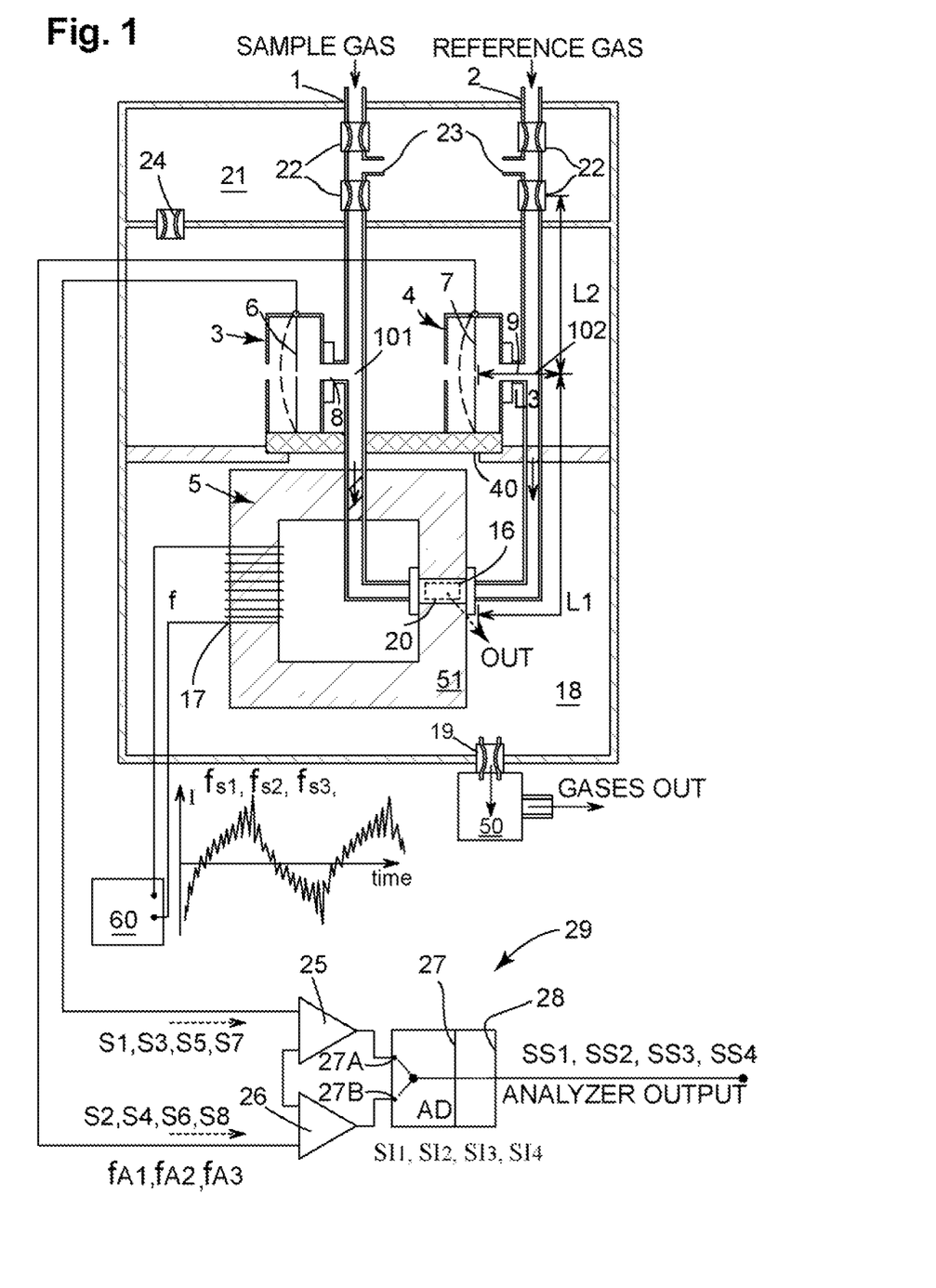
FIG. 1 shows a preferred arrangement for measuring the content of at least two gas components in gas mixture according to the invention.

In the first embodiment the gas analyzer has at least two pressure detecting microphones 3, 4, as shown in FIG. 1, the electronics 29 comprises at least a multi-channel electrical/electronic subtraction or addition unit 27 with optional amplifiers 25, 26, whose inputs $27_A$, $27_B$ are connected to receive at least two pairs of acoustic pressure signal components, i.e. the first signal component pair S1 and S2, and a second signal component pair S3 and S4, from the pressure detecting microphones. The electronics produces at least a subtraction/addition signal respective to each pair of acoustic pressure signal components at their acoustic measuring frequencies $f_{A1}$, $f_{A2}$ as the intermediate output signals $SI_{A1}$, $SI_{A2}$. In the second embodiment the gas analyzer has one pressure detecting microphone, not shown in the figures, said electronics 29 comprises at least an amplifiers 25, 26, whose input is connected to receive at least two acoustic pressure signal components, i.e. signal component S1 or S2, and signal component S3 or S4, from the pressure detecting microphone, and which produces at least a signal respective to each acoustic pressure signal component at their acoustic measuring frequencies $f_{A1}$, $f_{A2}$ as the intermediate output signals $SI_{A1}$, $SI_{A2}$.

The electronics 29 further comprises a calculation unit 28 having components that provide a first difference $\Delta SI_1$ between the second and first intermediate output signals $SI_{A2}$ and $SI_{A1}$ at their acoustic measuring frequencies $f_{A2}$ and $f_{A1}$ describing the content of said another gas component in the sample gas. Said calculation unit 28 may also comprise means providing a second difference $\Delta SI_2$ between the third and first intermediate output signals $SI_{A3}$ and $SI_{A1}$ at their acoustic measuring frequencies $f_{A3}$ and $f_{A1}$ describing the content of said third gas component in the sample gas.

According to the second aspect of the invention it is provided a method for analyzing at least a paramagnetic gas component in a sample gas, whereupon: a cyclically variable magnetic field in an air gap 16 positioned between opposing magnetic poles of an electromagnet 5 is created; said sample gas is allowed to flow along a sample gas conduit 1 into said air gap; a reference gas with known concentration of a predetermined gas component is allowed to flow along a reference gas conduit 2 into said air gap; said sample gas and said reference gas are allowed to intermix in said air gap under the effect of said variable magnetic field, and said intermixed gases are allowed to exit from said air gap through an exit conduit 18, 19; gas pressures at a first predetermined acoustic measuring frequency $f_{A1}$ are sensed from said sample gas conduit 1 and from said reference gas conduit 2 utilizing pressure detecting microphone or microphones 3, 4 giving at least one acoustic pressure signal component S1 and/or S2;

and calculations are applied to said acoustic pressure signal component or components forming at least a first intermediate output signal $SI_A$, describing content of a first gas component in the sample gas. Especially in addition: gas pressures at a second predetermined acoustic measuring frequency $f_{A2}$ are sensed from said sample gas conduit 1 and from said reference gas conduit 2 utilizing said pressure detecting microphone or microphones 3, 4 giving at least a second acoustic pressure signal component S3 and/or S4; and calculations are applied to said second acoustic pressure signal component or components forming at least a second intermediate output signal $SI_{A2}$ including content data of another gas component in the sample gas.

The at least two different magnetic field frequencies $f_{M1}$, $f_{M2}$, or a plurality of different magnetic field frequencies $f_{M(N+1)}$ are fed to the air gap with the electromagnet, whereupon the set of magnetic field frequencies shall include those frequencies, i.e. acoustic measuring frequencies $f_{A(N+1)}$, which are used for measuring the contents/concentrations of the predetermined gas components in the sample gas. In the case the gas analyzer has two pressure detecting microphones 3 and 4, the first acoustic pressure signal components S1 and S2 at said first acoustic measuring frequency $f_{A1}$ are subtracted from or added to each other resulting to said first intermediate output signal $SI_{A1}$; the second acoustic pressure signal components S3 and S4 at said second acoustic measuring frequency $f_{A2}$ are subtracted from or added to each other resulting to said second intermediate output signal $SI_{A3}$; and the third acoustic pressure signal components S5 and S6 at said third acoustic measuring frequency $f_{A3}$ are subtracted from or added to each other resulting to said third intermediate output signal $SI_{A3}$. In case the gas analyzer has one pressure detecting microphone, e.g. a differential microphone, the first acoustic pressure signal component S1 or S2 at said first acoustic measuring frequency $f_{A1}$ provides said first intermediate output signal $SI_{A1}$; the second acoustic pressure signal component S3 or S4 at said second acoustic measuring frequency $f_{A2}$ provides said second intermediate output signal $SI_{A3}$; and the third acoustic pressure signal component S5 or S6 at said third acoustic measuring frequency $f_{A3}$ provides said third intermediate output signal $SI_{A3}$.

The concentration of the first gas component, typically oxygen, is attained from said first intermediate output signal $SI_{A1}$ generally in a straightforward way. The concentration of the second gas component is attained from a first difference $\Delta SI_1$, which is a subtraction between the second and first intermediate output signals $SI_{A2}$ and $SI_{A1}$ at their acoustic measuring frequencies $f_{A2}$ and $f_{A1}$; And the concentration of the possible third gas component is attained from a second difference $\Delta SI_2$ being a subtraction between the third and first intermediate output signals $SI_{A3}$ and $SI_{A1}$ at their acoustic measuring frequencies $f_{A3}$ and $f_{A1}$.

DESCRIPTION OF THE PREFERRED EMBODIMENTS

Figure 2:
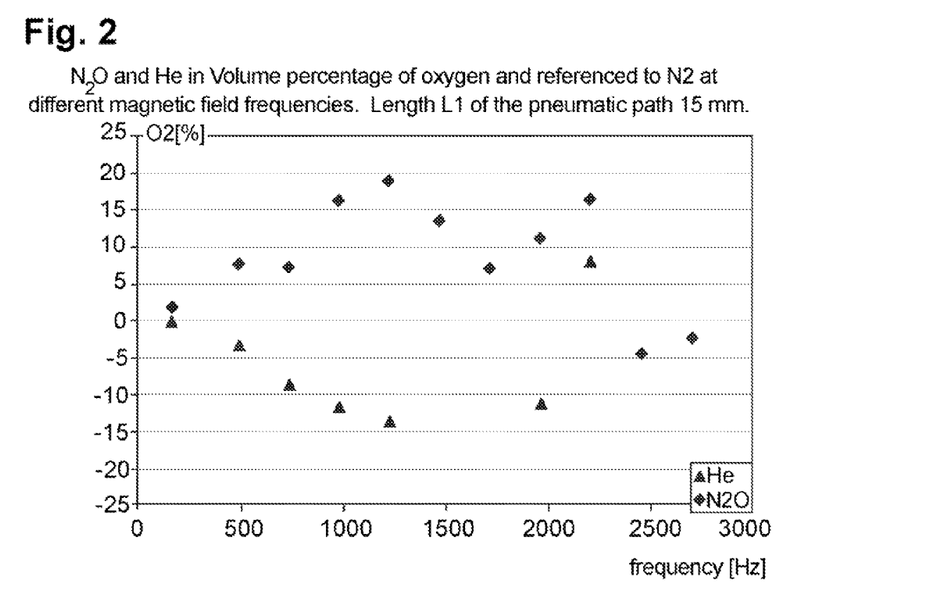
FIG. 2 shows the magnitude of the signal "error" relative to magnetic field frequency and the corresponding acoustic measuring frequency caused by $N_2O$ and He in volume percentage of oxygen in one prototype analyzer according to the invention.

The oxygen $O_2$ measurement is rather accurate at lower magnetic field frequencies and thus it is rather insensitive for the gases other than oxygen in the gas mixture. However the sensitiveness for gases other than oxygen rapidly increase as the magnetic field frequency is increased causing a rather large error to the oxygen measurement signal, which is proportional to the content of the gas other than oxygen in the mixture. For example commonly used breathing gases such as nitrous oxide $N_2O$ and helium He cause a minor or a negligible error to the oxygen measurement signal at lower magnetic field frequencies between 100-300 Hz, but the error rapidly increases as the magnetic field frequency is increased above 500-700 Hz. FIG. 2 shows the magnitude of the mentioned signal error relative to magnetic field frequency, i.e. the corresponding acoustic measuring frequency, caused by $N_2O$ and He in volume percentage of oxygen as oxygen is referenced to $N_2$ in one of the prototype analyzers of the invention. At lower frequencies, for example 100-300 Hz, the error caused by $N_2O$ is normally between 0.5-1.5% in volume percentage of oxygen and the error caused by He is 0-1% in volume percentage of oxygen, but it depends on the pneumatic construction of the analyzer also. As the error caused by the gases other than oxygen increases or decreases strongly at some frequencies, such as He and $N_2O$ causing an error even up to ±25% in volume percentage of oxygen, it is possible to measure the magnitude of the mentioned error by subtracting the two intermediate output signals of acoustic pressures at different magnetic field frequencies, i.e. the corresponding acoustic measuring frequency, such that error=$SI_{A2}$-$SI_{A1}$, where $SI_{A1}$ is the intermediate output signal measured at a lower magnetic field frequency with a negligible error in respect to oxygen, for example between 100 Hz and 300 Hz, and $SI_{A2}$ is the intermediate output signal measured at a higher magnetic field frequency, for example above 500 Hz, where the magnitude of the error included in to the acoustic pressure signal in respect to oxygen is larger or the largest. If there is only one gas component other than oxygen in the measured gas mixture the error signal is directly proportional to the content of the gas causing the error, but in the case there is more than one gas other than oxygen in the mixture the magnitude of the error is proportional to the combined effect of all the gases. Accordingly, the "error(s)" in signal is not really an error, but starting value(s) for determining the concentration of other gas components in the sample gas.

As can be seen from FIG. 2 the behavior of the "error" magnitude caused by He is different compared to the "error" magnitude caused by $N_2O$ at different magnetic field frequencies. Approximately at the magnetic field frequency $f_{A2}$ of 2200 Hz the "error" caused by He is zero, but the "error" caused by $N_2O$ at the same frequency is approximately 15 volume percents of oxygen. Slightly higher, approximately at the magnetic field frequency $f_{A3}$ of 2450 Hz, the "error" caused by $N_2O$ is in turn zero, but the "error" caused by He at that same frequency is now between 15-20 volume percents of oxygen. Thus by measuring the acoustic pressure signal at three different frequencies, in this specific case shown in FIG. 2, it is possible to determine the content of all three gas components $O_2$, He and $N_2O$ present in the sample gas mixture by subtracting the true intermediate output signal $SI_{A1}$ of oxygen measured at the lower frequency $f_{A1}$ below e.g. 300 Hz from the intermediate output signals $SI_{A2}$ for $N_2O$ and $SI_{A3}$ for He measured at respective acoustic measuring frequencies of $f_{A2}$=2200 Hz and $f_{A3}$=2450 Hz. As the gas content of $O_2$ is proportional to the intermediate output signal $SI_{A1}$, whereupon $CONTENT_{O2}=k_{O2}\cdot|SI_{A1}|$, the gas content of $N_2O$ is thus $CONTENT_{N2O}=k_{N2O}\cdot|SI_{A2}-SI_{A1}|$ and the gas content of He is thus $CONTENT_{He}=k_{He}\cdot|SI_{A3}-SI_{A1}|$, i.e. the first difference $\Delta SI_1=|SI_{A2}-SI_{A1}|$, and the second difference $\Delta SI_2=|SI_{A3}-SI_{A1}|$, and possible third difference $\Delta SI_3=|SI_{A4}-SI_{A1}|$, and so on depending on the number of gas components in the sample gas mixture. Constants $k_{N2O}$ and $k_{He}$ are gas specific multipliers to adjust the magnitude of the signal of that specific gas in to the same volume percentage scale with oxygen $O_2$, and $k_{O2}$ is a respective correction term if needed. In generalized form, i.e. for gas components G1, G2 and G3 with respective acoustic measuring frequencies of $f_{A1}$, $f_{A2}$ and $f_{A3}$, these equations can be written as follows: $CONTENT_{G1}=k_{G1}\cdot|SI_{A1}|$, $CONTENT_{G2}=k_{G2}\cdot|SI_{A2}-SI_{A1}|$ and $CONTENT_{G3}=k_{G3}|SI_{A3}-SI_{A1}|$ etc. the lower indices $_{A1}$, $_{A2}$, $_{A3}$, $_{A4}$ referring to the acoustic measuring frequency in question.

It is possible to measure the gases different than oxygen in the gas mixture by supplying an electrical current/voltage from the power source 60 to the electrical coil 17 of the electromagnet 5, which current/voltage is a combination or a sum of two or more alternating electrical currents/voltages having different frequencies $f_{(N+1)}$ (N=0, 1, 2 . . . ). Proportional to each electrical current/voltage frequency the magnetic field in the single air gap 16 of the electromagnet 5 has corresponding first harmonic frequency components at frequencies $f_{M(N+1)}=f_{(N+1)}$ (N=0, 1, 2 . . . ). Similar to the harmonic frequencies of the magnetic field the acoustic pressure signal components to be detected by the acoustic microphones 3 and 4 also have their harmonic frequencies. By determining a magnetic field frequency $f_{M(N+1)}$ for each specific gas components other than oxygen, and feeding an electrical current/voltage to the electrical coil of the electromagnet, which current/voltage includes at least such frequencies that create said determining a magnetic field frequencies in the air gap of the electromagnet, the response of the acoustic pressure signal detected by the acoustic microphones at corresponding acoustic measuring frequencies $f_{A(N+1)}$ thus includes the information of the gas content for that specific gas.

It shall be noted that the harmonic frequencies of the magnetic field depends on whether the electrical current/voltage, which has so called source frequencies $f_S$ induced in the power source 60, and thus the magnetic field in the air gap is unipolar or bipolar. When the magnetic field is unipolar the acoustic pressure signal detected by the acoustic microphones has its first harmonic frequency components at frequencies $f_{A(N+1)}=f_{M(N+1)}=f_{S(N+1)}$ (N=0, 1, 2 . . . ). When the magnetic field is bipolar the acoustic pressure signal detected by the acoustic microphones has its lowest first harmonic frequency component at the frequency $f_{A1}=f_{M1}=2\cdot f_{S1}$ (N=0), but the rest of the frequency components at higher frequencies have first harmonics at $f_{A(N+1)}=f_{M(N+1)}=f_{S(N+1)}$ (N=1, 2 . . . ). The lowest magnetic field frequency $f_{M1}$ (N=0) corresponding to the source frequency $f_{S1}$ in the unipolar case, and the source frequency $2\cdot f_{S1}$ in the bipolar case, where the sensitivity to oxygen is the highest, is called the first magnetic field frequency, which corresponds the first acoustic measuring frequency $f_{A1}$. At higher frequencies where the sensitiveness to gases other than oxygen is significant the magnetic field frequency $f_{M(N+1)}$ (N=1, 2 . . . ) can be called with a prefix second (N+1=2), third (N+1=3), fourth (N+1=4) . . . depending on the order of the frequency (N+1). Thus for example the magnetic field frequency $f_{M(1+1)}$ (N=1) is the second magnetic field frequency $f_{M2}$ corresponding the second acoustic measuring frequency $f_{A2}$, and the magnetic field frequency $f_{M(2+1)}$ (N=2) is the third magnetic field frequency $f_{M3}$ corresponding the third acoustic measuring frequency $f_{A3}$. And so on.

It is also possible to measure the oxygen content at the lower frequency $f_{A1}$ continuously, but the gas(es) other than oxygen are measured at higher frequencies $f_{A(N+1)}$ (N=1, 2, 3 . . . ) by switching the magnetic field frequency from one frequency to another and measuring the acoustic pressure signal at each corresponding switched frequency in turns.

Figure 3:
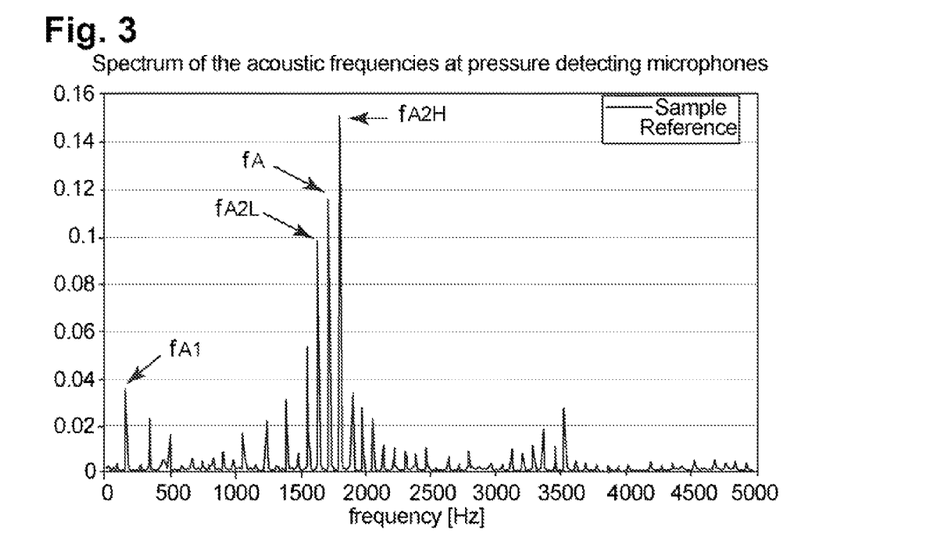
FIG. 3 shows the amplitude frequency spectrum of the acoustic frequencies at pressure detecting microphones.

It was mentioned earlier that it is also possible to measure the oxygen and two or even three different gases other than oxygen with a sum of only two source frequencies. The true oxygen signal can still be measured at the first harmonic of the acoustic measuring frequency $f_{A1}$, but gases other than oxygen are now measured at the first harmonic of the second acoustic measuring frequency $f_{A2}$ and at least at the first subharmonic acoustic frequencies around it. Other subharmonic acoustic frequencies may also be used for measuring the gases other than oxygen, but the magnitude of the acoustic signal decreases rapidly making the measurement demanding as can be seen from the graph in FIG. 3, which shows the amplitude spectrum measured from the sample and the reference microphone signal outputs and calculated with the Fast Fourier Transformation (FFT). The first subharmonic acoustic frequencies around the first harmonic of the second acoustic measuring frequency are specified by the sum and the difference of the first and the second source frequencies, but the polarity of the electrical current/voltage affects to all acoustic frequencies once again. For example, if the first and the second source frequencies are both bipolar a higher first subharmonic acoustic measuring frequency $f_{A2H}$ can be found at the frequency close to the second acoustic measuring frequency $f_{A2}$, which is a sum of the first and the second source frequencies $f_{A2H}=f_{S1}+f_{S2}$. Similarly a lower first subharmonic acoustic measuring frequency $f_{A2L}$ can be found at the frequency close to the second acoustic measuring frequency $f_{A2}$, which is a difference of the second and the first source frequencies $f_{A2L}=f_{S2}-f_{S1}$. The frequency difference between the two of these second harmonics $f_{A2L}$ and $f_{A2H}$ is thus $2f_{S1}$ or in terms of magnetic field frequency $f_{M1}$.

A functional measurement and adequate current/voltage and output signal magnitudes can be achieved by at first specifying the acoustic frequency for each specific gas other than oxygen to be measured, which was explained earlier and referred to FIG. 2, and:

In the case of using multiple source frequencies each higher source frequency $f_{S2}$, $f_{S3}$ etc. and each higher acoustic frequency $f_{A2}$, $f_{A3}$ etc. corresponding to those are adjusted to predetermined frequencies corresponding to each specific gas other than oxygen to be measured.

In the case when the higher source frequency is switched from one frequency to another in turn by turn, each switched higher source frequency and the acoustic frequency corresponding to that are specific for each gas other than oxygen to be measured.

In the case of using only two source frequencies $f_{S1}$ and $f_{S2}$, but the acoustic pressure signals are measured at the first harmonic of the higher acoustic frequency $f_{A2}$ and at the first subharmonics $f_{A2L}$ and $f_{A2H}$ around it, the second acoustic measuring frequency and the first subharmonic frequencies around it are adjusted so that each of those frequencies $f_{A2}$, $f_{A2L}$ and $f_{A2H}$ are specified to each of the three gases other than oxygen to be measured. Thus each of the three higher acoustic measuring frequencies are more sensitive to some of the gases other than oxygen whereas the first acoustic measuring frequency is sensitive for $O_2$ only. The measurement is carried out by first adjusting the first harmonic of the higher acoustic frequency $f_{A2}$ to the middlemost of the three frequencies predetermined for the three gases other than oxygen to be measured. As the first subharmonic frequencies $f_{A2L}$ and $f_{A2H}$ around the higher acoustic frequency $f_{A2}$ are determined by the difference and the sum of lower and higher source frequencies $f_{S1}$ and $f_{S2}$, the first subharmonic frequencies $f_{A2L}$ and $f_{A2H}$ are adjusted for the rest of the two gases other than oxygen by adjusting the lower source frequency $f_{S1}$ in the power source so that the first subharmonic frequencies $f_{A2L}$ and $f_{A2H}$ correspond to the predetermined frequencies of those two gases. With this method the adjusted frequencies of $f_{A2}$, $f_{A2L}$ and $f_{A2H}$ may not overlap exactly with the predetermined frequencies of the three gases other than oxygen, but with a combination of linear equations that can be derived from the specific data of three different gases other than oxygen that are measured at three different frequencies it is possible to solve the content of three unknown gases.

Even higher magnitudes at first subharmonics or other subharmonics of the higher acoustic frequency $f_{A2}$ can be achieved by adjusting the second source frequency $f_{S2}$ in the power source to a multiple of the first source frequency $f_{S1}$ in the power source.

Figure 4:
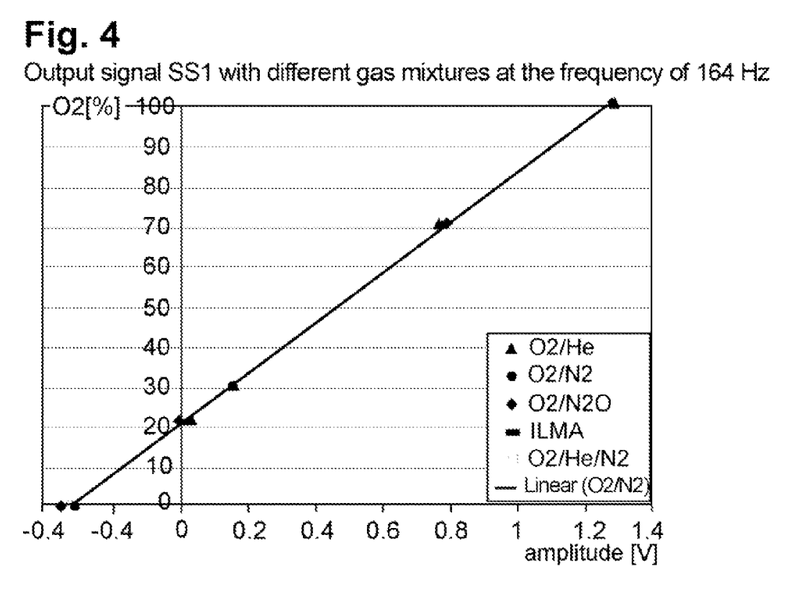
FIG. 4 shows the measured acoustic pressure signal with different gas mixtures at the magnetic field frequency and the corresponding acoustic measuring frequency of 164 Hz in the same prototype analyzer according to the invention.

In practice the first magnetic field frequency $f_{M1}$ and the respective acoustic measuring frequency $f_{A1}$ should be chosen as low as possible to avoid that oxygen measurement would have sensitiveness to other gases than oxygen. On the other hand the magnetic field frequency should be higher than 50 Hz and 60 Hz, which is used in the electrical network, but also their subharmonic frequencies should be avoided. Furthermore the magnetic field frequency/acoustic measuring frequency should be higher than for example 100 Hz to avoid different noise sources at lower frequencies, such as 1/f noise, but also noise caused by sound and vibrations at lower frequencies in general. In the prototype analyzer of this invention the bipolar source frequency $f_{S1}$ was at 82 Hz and thus the magnetic field frequency $f_{M1}$ was at 164 Hz, which frequency is also the acoustic measuring frequency $f_{A1}$. FIG. 4 shows the measured acoustic pressure signal with different gas mixtures at the magnetic field frequency of 164 Hz. As can be seen the "error" caused by $N_2O$ and He in the gas mixture remains fairly small throughout the overall concentration range of oxygen. The acoustic measuring frequency $f_{A1}$ is also 164 Hz. It should be noted that in practice the acoustic measuring frequencies $f_{A(N+1)}$ (N=0, 1, 2 . . . ) can be the same as the magnetic field frequencies $f_{M(N+1)}$, in case all superimposed frequencies are used, or most typically are some of the magnetic field frequencies $f_{M(N+1)}$, in case only some of the harmonic/subharmonic frequencies are used. The different magnetic field frequencies $f_{M(N+1)}$ can be of course attained e.g. using several audio frequency generators (=multivibrators) or a multi-channel audio frequency generator producing sinusoidal waves of electrical voltage/current, and combining the attained frequencies to a superimposed set of frequencies. This is a little complicated system, but it can create same or different voltage/current amplitudes for various frequencies used. FIG. 1 shows inserted a combination of two frequencies fed from the power source 60 as an example. A more sophisticated way of attaining different magnetic field frequencies $f_{M(N+1)}$ is to use an audio frequency generator producing non-sinusoidal waves of electrical voltage/current, e.g. square wave or triangular wave, whereupon the basic frequency forms the first harmonic, and there is a lot of upper harmonics and subharmonics, as can be seen using Fourier-analysis of the wave forms. This alternative can create only different voltage/current amplitudes for various frequencies used, but this is no problem because the signals attained from the differential microphone or two separate microphones must be anyway calibrated.

Figure 5:
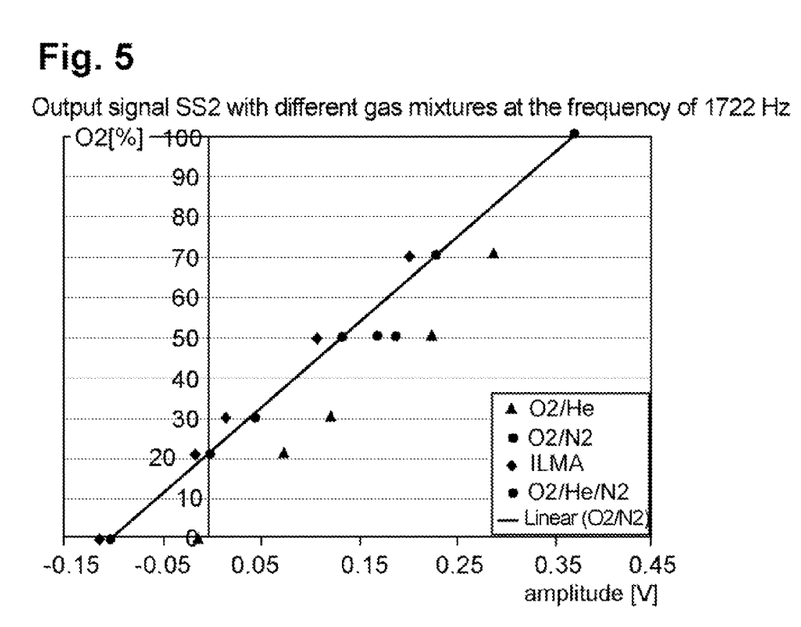
FIG. 5 shows the measured acoustic pressure signal with different gas mixtures of $O_2$, He, $N_2O$ and $N_2$ at the magnetic field frequency and the corresponding acoustic measuring frequency of 1722 Hz in the same prototype analyzer according to the invention.
Figure 6:
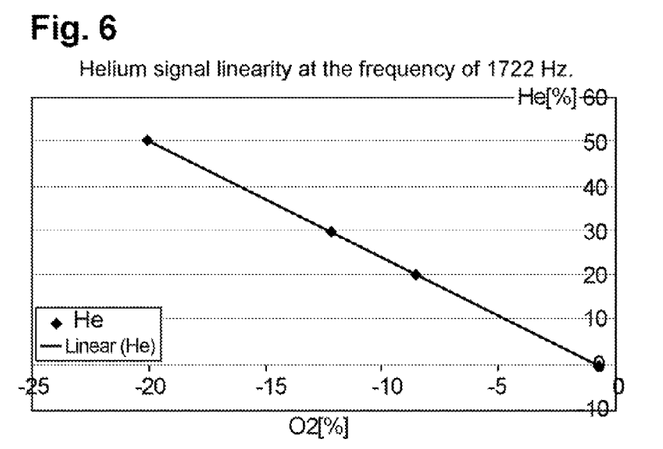
FIG. 6 shows a measured graph of the signal linearity caused by the Helium at the magnetic field frequency and the corresponding acoustic measuring frequency of 1722 Hz in the same prototype analyzer according to the invention.

In available commercial electromagnets the use of the higher magnetic field frequencies are limited below e.g. 5 kHz, since the electrical power losses and the sensor temperature increase proportionally to the magnetic field frequency. This in turn decreases the amplitude of the measured acoustic pressure signal correspondingly. The second magnetic field frequency $f_{M2}$ for the desired interfering gas, which in this case was Helium, was measured at the acoustic measuring frequency $f_{A2}$ of 1.722 Hz as the acoustic pressure signal S1, S2 deviation between the first and the second acoustic measuring frequency was the highest—refer to FIG. 2. FIG. 5 shows the measured acoustic pressure signal with different gas mixtures of $O_2$, He, $N_2O$ and $N_2$ at the magnetic field/acoustic frequency of 1722 Hz. As can be seen the "error" caused by $N_2O$ and He in the gas mixture at this specific magnetic field frequency, when referred to $O_2/N_2$ pair, is fairly large, below 70 volume percent concentration of oxygen, but the signal "error" decreases and finally approaches zero as the concentration of oxygen in the gas mixture is increased. Normally the concentration of oxygen in the breathing gas used in anesthesia or lung therapy is between 20-50 volume percent of oxygen simply for the safety reasons, though in some special cases 70 volume percent of oxygen can be used, but this is a maximum. Thus in practice the measurement of the gas content other than oxygen in the breathing gas mixture can be well implemented for the range of 30-80 volume percent, where the signal sensitivity and the resolution are adequate enough. FIG. 6 shows a measured graph of the signal linearity of Helium at the magnetic field frequency of 1722 Hz. The concentration of oxygen in the gas mixture is constant at 50 volume percent whereas the concentration of He has been changed from 0 to 50 volume percent, which is shown on the vertical axis in the graph in FIG. 6. $N_2$ is used as a balance gas and results are referenced to that. The magnitude of the error caused by He is shown on the horizontal axis in volume percentage of Oxygen. As can be seen from the FIG. 6 the measurement of He in the gas mixture of $O_2$ and $N_2$ is very linear within the concentration range of 0- to 50-volume percentage of He. The signal magnitude and the signal resolution are also high as 50 volume percentage of He in the mixture causes an signal error of more than 20% in volume percentage of $O_2$.

The paramagnetic gas analyzer comprises the sample gas conduit 1 and the reference gas conduit 2 as inlets for gases or gas mixtures, which gas conduits extend and open to an air gap 16 of an electromagnet 5. The sample gas is a gas mixture to be analyzed, and the reference gas has a predetermined or known concentration of a paramagnetic gas or some other gas. The electromagnet 5 has an electric coil 17 and a core 51 of ferromagnetic material that has spaced opposing magnetic poles forming the air gap 16 with a magnetic field therebetween. The gas analyzer comprises power source 60 for supplying either an alternating electrical current or a chopped direct electrical current to the electric coil 17 of the electromagnet 5, whereupon the magnetic field in the air gap varies respectively. Between the conduits 1 and 2 there is connected inlet pneumatic suppressors 22 as pressure equalizer, balancing openings 23 and a first common volume 21. There is an exit opening 20 from the air gap to a second common volume 18 for the mixed up reference and sample gases to remove the intermixed gases from the analyzer through an outlet pneumatic suppressor 19, and also a bypass suppressor 24 between the first and the second common volume 21 and 18. This is only one of the possible pressure equalizer arrangements, and it is possible to use other kinds of components and/or other kinds of arrangements, too. For attaining gas flows through the gas conduits 1, 2 there is fluctuation means 50, typically a pump arranged at the exit conduit after air gap exit opening 20, i.e. at said second common volume 18, or preferably at the outlet pneumatic suppressor 19, as shown in FIG. 1. The paramagnetic gas analyzer further comprises magnetic pressure sensing devices communicating with both gas conduits 1 and 2 through openings or passageways 8 and 9. Preferably these pressure sensing devices are pressure detecting microphones 3 and 4 connected to said sample gas conduit 1 and to said reference gas conduit 2, whereupon they sense gas pressures in the respective conduits, and give respective electrical pressure signals S1, S2. Accordingly, the microphones are for measuring the gas pressures within two conduits. There is also electronics 29 connected to said microphones to receive said electrical pressure signals S1, S2, S3 for further processing thereof. In the preferred embodiment there is two microphones in the gas analyzer, as shown in FIG. 1. The two microphones has parallel membranes 6, 7 and they are attached to a common body 40 or built in a common body to form an integrated microphone unit with two membranes. The other microphone is connected to the sample gas conduit and the other microphone is connected to the reference gas conduit, whereupon two acoustic pressure signal component, i.e. a pair of signal components, is received at each acoustic measuring frequency. In another embodiment there is only one differential microphones in the gas analyzer. The differential microphone has one membrane. The other side of this membrane is connected to the sample gas conduit and the other side of this membrane is connected to the reference gas conduit, whereupon one acoustic pressure signal component is received at each acoustic measuring frequency.

Figure 7:
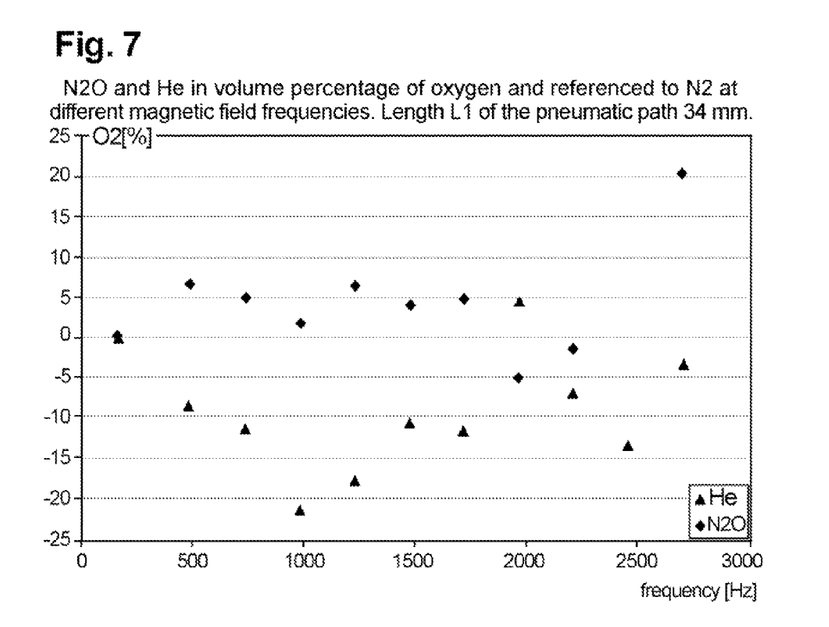
FIG. 7 shows sensitiveness dependence of the same prototype analyzer according to the invention in respect to gases other than oxygen over a frequency range with a different pneumatic path dimensioning.

The pneumatic path design between the single air gap 16 of the electromagnet, acoustic microphones 3 and 4 or a differential acoustic microphone, and pneumatic suppressors 22 also affect on the acoustic frequencies used for measuring gases other than oxygen. To minimize the measurement "error" at the first acoustic measuring frequency, the pneumatic paths between the magnetic air gap 16, acoustic microphones 3 and 4 connected to the sample gas conduit and reference gas conduit with a united signal processing, or a differential acoustic microphone like that schematically shown in the patent publication U.S. Pat. No. 4,633,705, and pneumatic suppressors 22 have to be symmetrical. Furthermore all the gas pockets, flow barriers, reductions, expansions, corners and turnings should be eliminated to increase the sensor response time, fall and rise times but also to decrease the sensitiveness to gases especially such as $N_2O$ and He, which together with pneumatic path asymmetry easily cause undesired measurement "error" at the first acoustic measuring frequency. This is achieved by minimizing the length L3 of the pneumatic path between the microphonic membrane 7, 6 and the intersection 102, 101 of the passageway 9, 8, and the reference gas conduit 2 and the sample gas conduit 1, as well as minimizing the volume of the measuring cavity 11, 10. The oxygen measurement at the first acoustic measuring frequency is somewhat insensitive to "error"s caused by the length of the pneumatic paths on condition that the pneumatic paths of the reference and the sample gas conduits remain symmetrical. However the dimensioning of the pneumatic path length changes the "error" sensitiveness or sensitiveness to gases other than oxygen at some higher frequencies. The sensitiveness to gases other than oxygen does not necessarily increase, but can also decrease and changes from point to point as the frequency is increased, as shown in the graph in FIG. 7. In addition, the temperature at least in the single air gap 16, and preferably in the system between the pneumatic suppressors 22 in the input gas conduits 1, 2 and the outer of the exit conduits 19, should be as homogenous as possible to avoid uncontrollable deviations caused by other phenomena than the magnetic susceptibility utilized for the invention. Normally there is anyway some warming up from different reasons, the effect of which shall be compensated. This compensation is not part of the invention, and accordingly, not explained in this text.

The signal response or the signal magnitude specific to each gas other than oxygen at a certain predetermined higher frequency can be adjusted by adjusting the length L1 of the pneumatic path between the magnetic air gap 16 and the intersection 102, 101 of the passageway 9, 8 and the reference and sample gas conduits 2, 1. As can be seen from FIGS. 2 and 6 the change of pneumatic path length L1 from 15 mm to 34 mm reshapes the signal response relative to frequency. At lower frequencies under 700 Hz He and $N_2O$ curves look very similar in FIGS. 2 and 6, but the behavior of the curves changes considerably as the frequency is increased over 700 Hz. It was found experimentally that the most suitable length L1 for the pneumatic path L1 in the prototype gas analyzer of this invention was 15 mm. The influence of the length L2 of the pneumatic path, between the pneumatic suppressor 22 and the intersection 102, 101 of the passageway 9, 8 and the reference and sample gas conduits 2, 1, to the signal response or the signal magnitude specific to each gas other than oxygen at a certain higher frequency was much lower in the prototype gas analyzer of this invention. However by changing the length L1 of the pneumatic path or by changing the proportions of lengths L1 and L2 of the pneumatic path, still keeping the sample and reference gas conduits symmetrical, it is possible to adjust the sensitiveness of the gas or gases other than oxygen or the proportions of magnitudes of those gases at the specific frequency or frequencies. It has to be also considered that the design of other components relating to pneumatic paths, such as suppressors 22 and magnetic air gap 16 etc. have an influence on the gas measurement at higher frequencies.

Electrical signals S1 to S8 from the acoustic microphone or microphones can be processed electronically, but more sophisticated and easier implementation can be achieved by digital processing. This can be done by converting the analogous signals from electrical outputs $3_E$, $4_E$ of acoustic microphones 3 and 4 in to the digital form by analog to digital converter in the subtraction/addition unit 27 after the electrical signals have been amplified to a sufficient voltage level by the optional pre-amplifiers 25, 26. Then the intermediate output signals $SI_{41}$, $SI_{42}$, $SI_{43}$ and possible $SI_{44}$ are also in digital form, whereupon they can be forwarded to a central processing unit, not shown in the figures, to process the measured data programmatically. The oxygen concentration, i.e. the first analyzer output signals $SS_1$, can be directly calculated from the first intermediate output signals $SI_{41}$, which in turn is directly calculated from the first pair of acoustic pressure signal components S1, S2 attained from microphone(s) at the first acoustic measuring frequency $f_{A1}$ that has the lowest frequency. Accordingly, calculation of oxygen concentration is quite straightforward. The concentration of gas or gases other than oxygen, i.e. the analyzer output signals $SS_2$, $SS_3$ and $SS_4$, can be calculated from the first intermediate output signals $SI_{A2}$, $SI_{A3}$, $SI_{A4}$, which in turn is directly calculated from the signal pairs of acoustic pressure signal components S3 and S4, S5 and S6, S7 and S8 attained from microphone(s) at the higher acoustic measuring frequencies $f_{A2L}$, $f_{A2}$ and $f_{A2H}$ by subtracting the first analyzer output signal $SI_{A1}$ from each of the intermediate output signals $SI_{A2}$, $SI_{A3}$, $SI_{A4}$ turn by turn. Analyzer output signals $SS_2$, $SS_3$ and $SS_{A4}$ behave differently for each gas mixture and give a different combination of signal magnitudes $SI_{A2}$, $SI_{A3}$, $SI_{A4}$, which are relative to the concentration of each gas or gases other than oxygen in the mixture. With a suitable system of equations the concentration of each gas other than oxygen can be calculated from the signals $SI_{A2}$, $SI_{A3}$, $SI_{A4}$ and transformed into the suitable representation.

What is claimed is:

1. A gas analyzer, comprising:
   an electromagnet that has spaced opposing magnetic poles forming an air gap with a magnetic field therebetween;
   a power source for supplying cyclically variable electrical current/voltage to said electromagnet;
   a sample gas conduit and a reference gas conduit opening into said air gap, said sample gas conduit carrying a sample gas comprising a gas mixture to be analyzed, and said reference gas conduit carrying a reference gas having a known concentration of a predetermined gas component;
   an exit conduit communicating with said air gap for removing an intermixed sample comprising said sample gas and said reference gas from said air gap with the magnetic field;
   a pressure detecting microphone connected to said sample gas conduit and to said reference gas conduit, said pressure detecting microphone adapted for sensing gas pressures at a first predetermined acoustic measuring frequency and a second predetermined acoustic measuring frequency; and
   electronics connected to said pressure detecting microphone to receive a first acoustic pressure signal component and a second acoustic pressure signal components, said electronics forming intermediate output signals comprising at least:
   a first intermediate output signal describing content of a paramagnetic gas component in the sample gas, and
   a second intermediate output signal including content data of a second gas component in the sample gas,
   wherein said electronics comprise an amplifier with an input connected to receive said first acoustic pressure signal component and said second acoustic pressure signal component,
   wherein said amplifier generates the first intermediate output signal and the second intermediate output signal,
   wherein said electronics comprise a calculation unit with means to provide a first difference to describe the content of a gas component in said sample gas, and
   wherein the first difference is calculated by subtracting the second intermediate output signal and the first intermediate output signal at their acoustic measuring frequencies.

2. A gas analyzer according to claim 1, wherein:
   said pressure detecting microphone is adapted for sensing gas pressures at a third predetermined acoustic measuring frequency; and
   said electronics receive a third acoustic pressure signal component, and form a third intermediate output signal including content data of a third gas component in the sample gas.

3. A gas analyzer according to claim 2, wherein said calculation unit comprises means to provide a second difference to describe the content of said third gas component in the sample gas, and wherein the second difference is calculated by subtracting the third intermediate output signal and the first intermediate output signal at their acoustic measuring frequencies.

4. A gas analyzer according to claim 3, wherein said calculation unit is adapted to provide at least two analyzer output signals starting from said first intermediate output signal, said first difference, and second difference, and wherein said analyzer output signals are proportional to the concentrations of three different gases present in said sample gas.

5. A gas analyzer according to claim 3, wherein said first acoustic measuring frequency, said second acoustic measuring frequency, and a third acoustic measuring frequency are selected to match for determination of the content of oxygen and/or helium and/or nitrous oxide.

6. A gas analyzer according to claim 2, wherein said first acoustic measuring frequency, said second acoustic measuring frequency, and a third acoustic measuring frequency are selected to match for determination of the content of oxygen and/or helium and/or nitrous oxide.

7. A gas analyzer according to claim 1, wherein said power source is a multi-frequency power source.

8. A gas analyzer according to claim 7, wherein said multi-frequency power source has components for supplying a chopped or alternating electrical current/voltage to said electromagnet to produce magnetic field frequencies in said air gap of the electromagnet, said magnetic field frequencies respective at least to said first and second predetermined acoustic measuring frequencies.

9. A gas analyzer according to claim 1, wherein:
   at least two pressure detecting microphones are connected to said sample as conduit and said reference gas conduit, and
   wherein said electronics comprises at least a multi-channel electrical/electronic subtraction or addition unit that has amplifiers with inputs connected to receive at least two pairs of acoustic pressure signal components from the pressure detecting microphones, and which produce at least a subtraction/addition signal respective to each pair of acoustic pressure signal components at their acoustic measuring frequencies as the intermediate output signals.

10. A method for analyzing at least a paramagnetic gas component in a sample gas, the method comprising:
    creating a cyclically variable magnetic field in an air gap positioned between opposing magnetic poles of an electromagnet;
    flowing a sample gas along a sample gas conduit into said air gap;
    flowing a reference gas with known concentration of a predetermined gas component along a reference gas conduit into said air gap;
    intermixing said sample gas and said reference gas in said air gap under the effect of said cyclically variable magnetic field, wherein said intermixed gases are allowed to exit from said air gap through an exit conduit;

sensing gas pressures at a first predetermined acoustic measuring frequency from said sample gas conduit and from said reference gas conduit utilizing a pressure detecting microphone giving at least a first acoustic pressure signal component;

sensing gas pressures at a second predetermined acoustic measuring frequency from said sample gas conduit and from said reference gas conduit utilizing said pressure detecting microphone giving at least a second acoustic pressure signal component;

applying calculations to said first acoustic pressure signal component forming at least a first intermediate output signal describing content of a first gas component in the sample gas;

applying calculations to said second acoustic pressure signal component forming at least a second intermediate output signal including content data of a second gas component in the sample gas; and calculating a first difference to describe the content of another gas component in said sample gas, wherein the first difference is calculated by subtracting the second intermediate output signal and the first intermediate output signal at their acoustic measuring frequencies, and wherein the first intermediate output signal and the second intermediate output signal generated by an amplifier from said first acoustic pressure signal component and said second acoustic pressure signal component.

11. A method according to claim 10, further comprising:

sensing gas pressures at a third predetermined acoustic measuring frequency from said sample gas conduit and from said reference gas conduit utilizing said pressure detecting microphone giving at least a third acoustic pressure signal component; and applying calculations to said third acoustic pressure signal component or components forming at least a third intermediate output signal including content data of a third gas component in the sample gas.

12. A method according to claim 11, further comprising:

selecting one of said second acoustic measuring frequency and said third acoustic measuring frequency that has a higher frequency for measuring the concentrations of oxygen and a gas or gases other than oxygen.

13. A method according to claim 12, wherein said second acoustic measuring frequency is selected to be in the order of 2000 Hz for determining the concentration of nitrous oxide as said second gas component, and wherein said third acoustic measuring frequency is selected to be in the order of 2450 Hz for determining the concentrations of helium third gas component.

14. A method according to claim 11, further comprising:

one of subtracting and adding the third acoustic pressure signal component at said third acoustic measuring frequency from or to each other resulting to said third intermediate output signal.

15. A method according to claim 14, further comprising attaining the concentration of the third gas component from a second difference, wherein the second difference is calculated by subtracting the third intermediate output signal and the first intermediate output signal at their acoustic measuring frequencies.

16. A method according to claim 10, further comprising:

selecting one of said first acoustic measuring frequency and said second acoustic measuring frequency that has a higher frequency for measuring the concentrations of oxygen and a gas or gases other than oxygen.

17. A method according to claim 16, further comprising:

selecting said first acoustic measuring frequency to be at a maximum 300 Hz for determination of the concentration of oxygen as said first gas component in the sample gas;

selecting said second acoustic measuring frequency to be in the order of 2200 Hz for determining the concentrations nitrous oxide as said second gas component; and selecting said third acoustic measuring frequency to be in the order of 2450 Hz for determining the concentrations of helium as said third gas component.

18. A method according to claim 10, further comprising:

one of subtracting and adding the first acoustic pressure signal component at said first acoustic measuring frequency from or to each other resulting to said first intermediate output signal; and one of subtracting and adding the second acoustic pressure signal component at said second acoustic measuring frequency from or to each other resulting to said second intermediate output signal.

19. A method according to claim 18, further comprising:

attaining the concentration of the first gas component from said first intermediate output signal; and attaining the concentration of the second gas component from the first difference.

20. A method according to claim 10, wherein the first acoustic pressure signal component at said first acoustic measuring frequency provides said first intermediate output signal, and wherein the second acoustic pressure signal component at said second acoustic measuring frequency provides said second intermediate output signal.

21. A method according to claim 20, wherein the third acoustic pressure signal component at said third acoustic measuring frequency provides said third intermediate output signal.

* * * * *